United States Patent [19]

Hwang et al.

[11] Patent Number: 4,885,051
[45] Date of Patent: Dec. 5, 1989

[54] OPTICALLY CONTROLLED DIMPLER FOR PREPARATION OF ULTRATHIN SAMPLES

[75] Inventors: Dah-min D. Hwang, Holmdel; Lawrence R. Nazar, Fair Haven, both of N.J.

[73] Assignee: Bell Communications Research, Inc., Livingston, N.J.

[21] Appl. No.: 324,318

[22] Filed: Mar. 16, 1989

[51] Int. Cl.$^4$ .................. H01L 21/306; B44C 1/22; C03C 15/00; C03C 25/06
[52] U.S. Cl. .................. 156/345; 156/636; 156/645; 156/662; 156/626
[58] Field of Search ............... 156/345, 626, 636, 637, 156/640, 645, 662, 903; 51/204, 206 R, 209 R, 317

[56] References Cited

U.S. PATENT DOCUMENTS

| | | | |
|---|---|---|---|
| 3,019,564 | 2/1962 | Haracz | 156/636 X |
| 4,588,473 | 5/1986 | Hisatomi et al. | 156/645 |
| 4,793,895 | 12/1988 | Kaanta et al. | 156/627 |

Primary Examiner—William A. Powell
Attorney, Agent, or Firm—James W. Falk; Charles S. Guenzer

[57] ABSTRACT

A dimpler for grinding a spherical dimple into and partially through a sample so as to form very thin portions of the sample around the perforation suitable for transmission electron microscopy. The sample is held on stage rotating about a vertical axis and a wheel rotating about a horizontal axis is brought into contact with the rotating sample. A first light path is formed across a diameter of the wheel and a second light path is formed vertically downward through the stage. A laser shines light downwardly to the rotating wheel so that the rotating wheel chops the light by the time it strikes the sample being ground. When the sample is perforated, a photodetector at the bottom of the second light path first detects the chopped light and immediately causes the grinding to halt by lifting the wheel away from the sample. The dimpling is performed by dripping an etchant onto a relatively soft wheel and the etchant is rinsed automatically upon perforation.

10 Claims, 7 Drawing Sheets

OPTICALLY CONTROLLED DIMPLER FOR PREPARATION OF ULTRATHIN SAMPLES

FIELD OF THE INVENTION

The invention relates generally to the preparation of thin portions of samples. In particular, the invention relates to the use of a dimpler in the preparation of ultrathin samples for subsequent analysis by transmission electron microscopy.

BACKGROUND OF THE INVENTION

Transmission electron microscopy (TEM) is becoming increasingly important in the characterization of semiconductor devices. One such application is in the recent developmental work of integrated semiconductor devices in which several layers of different materials are deposited and some of the layers may be only a few atoms thick. The dimensions of the lateral structures may be less than a fraction of 1 $\mu$m. In order to characterize these devices at these very small dimensions, TEM is felt to be necessary. For investigations of the structural variation with depth, it is necessary that the TEM be performed on a vertical cross-section of the device. However, because of the strong absorption of electrons in a solid, the necessary cross sections must have a thickness on the order of 50 nm and certainly no more than 200 nm.

Once well known method of preparing such thin cross-sectional samples involves ion milling a hole through a relatively thin sample. A wafer has fabricated thereon a surface layer structure. Fragments of the wafer are epoxied together with their structured surfaces facing each other. The thickness of the sample is then reduced in the direction extending along the epoxy by means of mechanical polishing. Therefter, the thinned sample is ion milled. The purpose is to form a small hole in the vicinity of the epoxy bond which will expose wedge-like cross sections of the surface structure.

However, this ion milling method suffers from the defect that it not only takes significant time to mill through a thickness sufficient to support a planar sample but also that the location of the perforation is difficult to control. The diameter of the ion beam is typically wider than the desired hole. The hole has a tendency to develop at a local defect within an area of the beam. Therefore, the hole may be centered off the epoxy. Ion milling necessarily involves high vacuum chambers and ion sources. Thus, the ion milling equipment is expensive. Ion milling involves projecting ions of at least a few keV of energy at the material. Such energetic ions not only sputter away the sample material but also produce a certain amount of subsurface damage in the area of the sample to be later analyzed by TEM. A further problem is that many materials, such as CdTe, are prone to damage and artifacts and therefore exotic types of ion milling are required, for example, reactive ion milling using iodine or chlorine ions. Such equipment is very specialized and very expensive.

In order to eliminate some of the problems of ion milling, a further step of dimpling has found widespread use. Dimplers are commercially available from Gatan Corporation of Pleasanton, Calif., VCR Group of San Franciso, Calif., and Southbay Technology of Temple City, Calif. A dimpler will be described in more detail later but can be generally described as a mechanical grinder which forms a spherical depression or dimple in the sample. In use for forming TEM samples, the dimpler forms a dimple in a relatively thick sample of the sort described before, that is, the two fragments epoxied together. The dimple extends to a depth such that the bottom of the dimple is in the area of the epoxy layer and the remaining thickness of the sample below the dimple is relatively thin. Thereafter, the ion milling is performed on the thin sample at the bottom of the dimple.

The dimpling provides two advantages. First, the portion of the sample away from the dimple is relatively thick and thus provides mechanical rigidity so that the minimum thickness at the bottom of the dimple can be made much thinner. Therefore, less ion milling is required to form the hole. Secondly and more importantly, the ion-milled hole will form at the thinnest portion of the sample. Therefore, if the epoxy layer is aligned with the center of the dimple, the hole will most likely form across the epoxy layer and in both of the wafer fragments. Hence, it is much more likely that a usable cross-sectional sample will be obtained for TEM.

Nonetheless, the combination of dimpling and ion milling suffers from many problems. The problems of the expense of ion millers and of compounds which are damaged or are unstable under ion milling remain. A common layered semiconductor structure of great interest involves III-V compounds such as InP. Much difficulty has been experienced in providing high quality cross-sectional samples of InP for TEM.

The dimpler is a relatively simple mechanical device which is inexpensive and easy to operate. In its present form, it significantly improves the utility of ion milling but does not overcome the difficulties and expense inherent in ion milling.

Another conventional method of perforating metal foils and crystalline slices is jet-thinning. In this method, a stream of corrosive fluid is directed at the specimen until perforation occurs. Bromine or chlorine in methanol is well known for polishing planar samples of compound semiconductors and has further been used in jet thinning. An extension of this idea involves electro-polishing when the corrosive action of the fluid is enhanced or supplanted by electrolytic ablation. In any case, jet thinning has never been successfully applied to producing cross-sectional TEM samples.

SUMMARY OF THE INVENTION

Accordingly, an object of the invention is to provide a method and apparatus for preparing a sample for cross-sectional transmission electron microscopy.

A further object is to provide such a method and apparatus which can create a hole in a thin sample, which hole has a well defined location and sharp edges.

A yet further object is to provide such a method and apparatus which avoids the use of ion milling.

The invention can be summarized as an improved dimpler and use thereof in which an optical path is provided through a grinding wheel of the dimpler and the support for the sample. When the grinding wheel has penetrated the sample and forms a hole therethrough, so that light shines through the hole, grinding is immediately halted. For a sample composed of a III-V or II-VI semiconductor, dimpling is chemically performed by dripping a bromine-methanol etchant over a plastic grinding wheel.

DETAILED DESCRIPTION

First, the prior art procedure for ion milling and dimpling combined with ion milling will be described in more detail.

Figure 1:
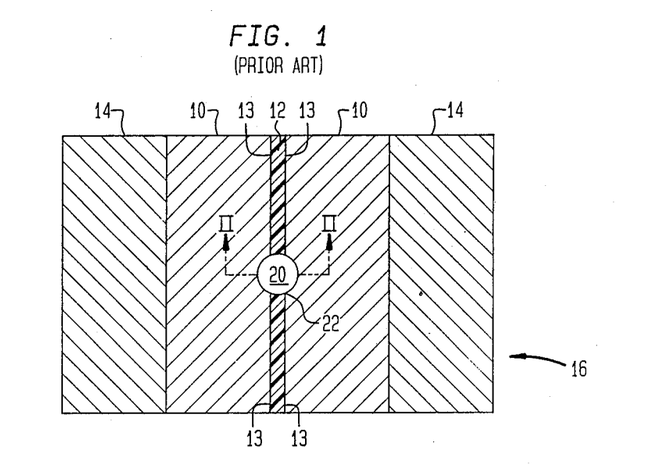
FIG. 1 is a plan view of a sample prepared for cross-sectional TEM according to the prior art.
Figure 2:
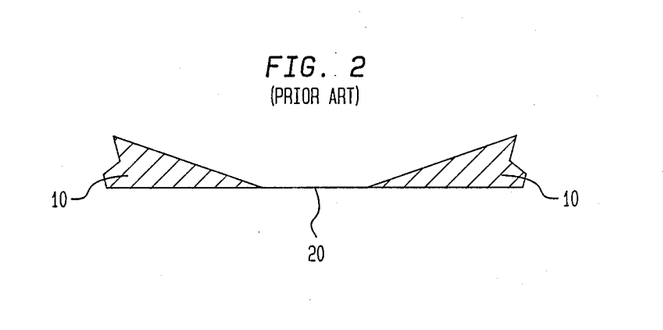
FIG. 2 is a cross-sectional view of the sample of FIG. 1 taken along section II—II.

A wafer has formed on its surface the surface structure for which a TEM cross-section is desired. The wafer is then scribed and diced to form small wafer fragments or sample dies 10, as illustrated in FIG. 1. Two such sample dies 10, each having the same surface layer structure are bonded together by an epoxy layer 12. The surface layer structure is on a side 13 of each die 10 facing the epoxy layer 12. The thickness of the epoxy layer 12 is exaggerated in the figure. The outsides of the sample dies 10 are then bonded to support dies 14 which provide better mechanical support. The thus assembled sample dies 10 and support dies 14 form a sample 16 which is then ground and polished so that the thicknes of the sample 16 in the direction perpendicular to the illustration of FIG. 1 is uniform and thin, on the order of less than 100 $\mu$m and perhaps as little as 30 $\mu$m. Thereafter, the so thinned sample 16 is ion milled by two small opposing beams focused on opposite sides in the vicinity of the epoxy layer 12, that is, over both of the structured layer sides 13. The result is the boring of a generally circular hole 20 through the structure. The ion milling machine typically contains a light source which is focused on the area being milled. A light detector on the opposite side of the sample then detects any light transmitted through a newly opened hole and immediately stops the ion milling. The circularity of the hole 20 is exaggerated in the FIG. 1 and in most cases the hole 20 assumes a jagged shape. Importantly, it has been found that the hole 20 is bored such that, as illustrated in FIG. 2, the thickness of the sample dies 10 adjacent the hole 20 increases gradually away from the hole 20. Therefore, there are four areas 22 on the periphery of the hole 20 and immediately adjacent the epoxy layer 12 which are both ultrathin and which provide a cross-section of the surface of either one of the sample dies 10.

Figure 3:
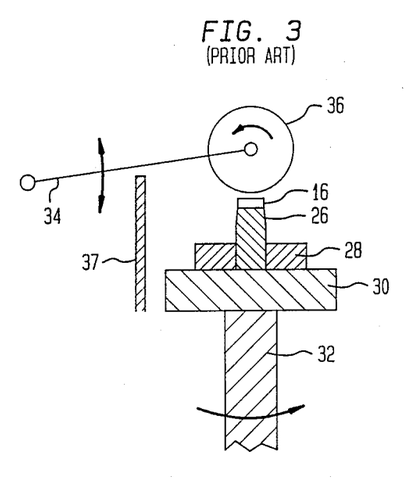
FIG. 3 is a pictorial view of a conventional dimpler.
Figure 4:
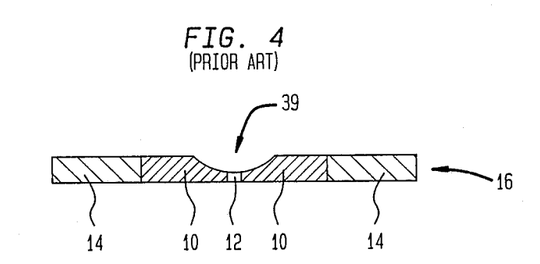
FIG. 4 is a cross-section of a dimpled sample prepared with the conventional dimpler of FIG. 3.

As described previously, the use of ion milling alone is disadvantageous and dimpling followed by ion milling is conventionally preferred. A prior art dimpler is illustrated schematically in FIG. 3. The sample 16 is first bonded to the end of a stainless-steel dimpler pin 26. The bonded sample 16 is then ground flat and polished to have a relatively large thickness of about 100 $\mu$m. The dimpler pin 26 with the ground sample 16 is slide fitted into a hole of a pin fixture 28. The pin fixture 28 is selectively positioned on the surface of a rotatable table or dimpler stage 30 to which it is magnetically coupled. The stage 30 is mounted on a shaft 32 which is rotated by an unillustrated motor. A rotatale arm 34 has mounted on its free end a grinding wheel 36 which is driven to rotate by another unillustrated motor. Selective amounts of down pressure are provided by conventional unillustrated means. The lowest position of the arm 34, and thus of the grinding wheel 36, is determined by a precision screw detente 37. Usually, the grinding wheel 36 rotates about an axis extending along the arm 34, that is, the arm 34 is the shaft of the grinding wheel 36. The components are positioned so that when the arm 34 brings the grinding wheel 36 into contact with the sample 16, the contact point lies on the rotation axis of the shaft 32. The grinding wheel 36 is in fact a series of wheels of decreasing hardness as is typical in a grinding and polishing procedure. The harder wheels have an axial cross-section at their circumference of a curvature equal to the main circumferential curvature. Therefore, the harder wheels grind a spherical dimple 39, as illustrated in FIG. 4, into the surface of the sample 16. The softer wheels, such as the felt ones, need not be specially shaped since they conform to the already ground dimple 39. The rotation of the dimpler stage 30 and thus of the sample 16 during grinding provides further uniformity. The grinding and polishing is considered to be purely mechanical and utilizes grinding compounds such as alumina and diamond slurries for the rough grinding.

The sample 16 is spherically ground such that the minimum thickness of the dimpled sample 16, at the bottom of the dimple 39, is about 10 $\mu$m. Optionally, a second dimple may be formed on the opposite side of the sample 16. Thereafter, the sample 16 is subjected to the type of ion milling described above. The grinding is stopped at 10 $\mu$m instead of being continued to TEM thicknesses because control of the final thickness is difficult. Control of thicknesses to about $\pm 5$ $\mu$m is the currently available limit.

The present invention dispenses with the use of ion milling and relies completely upon the dimpler for forming the TEM cross-sectional sample. However, the dimpler must be precisely controlled and is therefore of a novel design. The dimpler of the invention uses optical control of the grinding wheel of dimpler so that grinding can be precisely stopped just as the sample is penetrated. Thereby, the ion milling becomes unnecessary. An optical path is provided through the rotating grinding wheel and the transversely rotating support holding the sample. The invention can be practiced on a modification of the dimpler Model 656-0000, sold by Gatan, but other dimplers can also be so modified.

Figure 5:
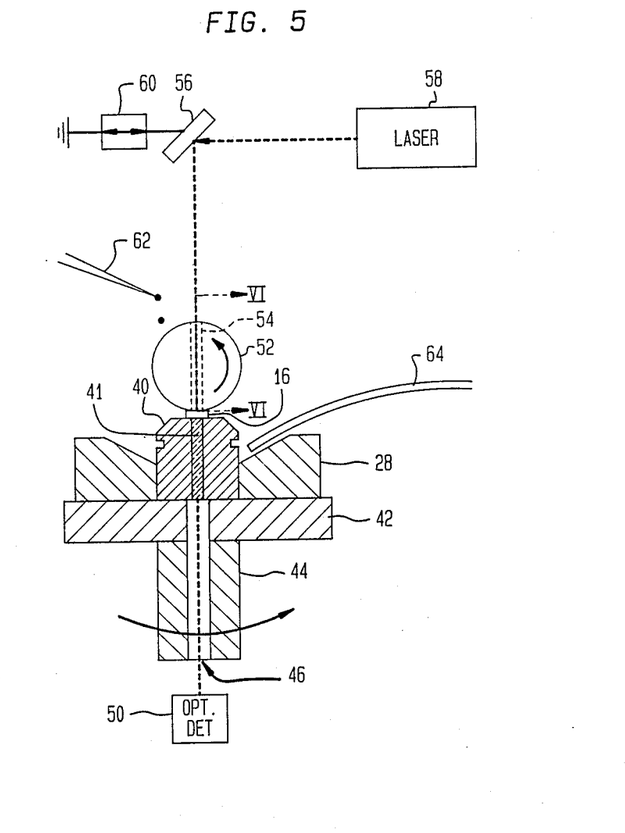
FIG. 5 is an illustration, partially in cross-section, of the dimpler of the present invention.

As illustrated in FIG. 5, the sample 16 is mounted on a stainless steel dimpler pin 40 having a glass insert 41 and insertably held by the pin fixture 28. The pin fixture 28 is magnetically and slidably held to a rotating dimpler stage 42, which is composed of a ferromagnetic material and is rotated by a shaft 44. The stage 42 and shaft 44 have bored therethrough an axial light passage 46. Any light shining vertically through the sample 16 will be detected by an upwardly facing optical detector 50. The shaft and motor in the Gatan conventional dimpler are replaced by a belt-drive system to provide for the unobstructed optical path. It is noted that some recently designed dimplers provide for a similar optical path beneath a sample mounted on the dimpler pin so that the motor modifications would not then be required. In these recent dimplers, a light source shines on the bottom of the sample being dimpled. With this apparatus, the grinding wheel can be moved out of the way during an interruption of the grinding in order to allow a visual inspection by the operator of whether a perforation has occurred.

In the dimpler of the present invention, a grinding wheel 52 with a grinding surface in the shape of a band of a sphere has formed therein a diametric optical bore 54. Twice each revolution of the wheel 52, light reflected by a mirror 56 from a laser 58 shines through the optical bore 54 and is thereby chopped at twice the grinding wheel frequency. In operation, the grinding wheel 52 is brought into rotating contact with the transversely rotating sample 16 and is then biased downwardly with a predetermined small force by conventional means associated with the dimpler. As soon as the grinding wheel 52 has ground a tiny perforation through the sample 16, the chopped light is detected by the optical detector 50. If the positions of the laser 58 and the detector 50 are reversed, there arises the problem of ambient light entering the detector 50.

The laser 58 may be a 2 mW HeNe laser conveniently mounted on the ceiling of a fume bond in which the dimpler is placed. The laser output is focused by a 40 cm lens onto the overhead mirror 56, which is attached to the ceiling by a three-dimensional translator 60 so as to position the laser light on the plastic grinding wheel 52. The above optical elements are conveniently mounted on an optical rail attached to the hood ceiling.

The modified dimpler can be advantageously used in conjunction with chemical rather than mechanical grinding to thereby provide a smoothly grounds ample. In chemical dimpling, a etchant is supplied by a drawn-glass drip tube 62 and dripped onto the rotating grinding wheel 52. Excess etchant is sucked away by a pipette 64 connected to an aspirator. At the termination of etching, the sample 16 is flushed with methanol supplied through an, as yet unillustrated, pressurized needle jet. The etchant supply may be turned off manually thereafter. In chemical dimpling, the wheel 52 may be of plastic, such as delrin, as supplied by Gatan, of Nylon or of other materials resistant to the etchant. The grinding wheel 52 should be of a material which is of ordinary hardness and self-lubricating so as not to in fact perform any mechanical grinding of the sample 16. It is possible that the plastic grinding wheel 52 performs the entire dimpling process since it is the etchant rather than the grinding action of the grinding wheel 52 which removes the sample material. Therefore, no multi-stage polishing is required.

We have found that a bromine and methanol solution performs adequate etching for a wide variety of III-V and II-VI semiconductor compounds when used with the plastic grinding wheel in a dimpler. The strength of the solution should be in the range of 0.1 to 1% of liquid bromine to methanol by volume. One drop of liquid bromine in 100 cc corresponds to about 0.04%. We found that if we added enough concentrated bromine to methanol to form a yellow-orange solution, the strength was adequately controlled for use with the invention.

The drip rate onto the plastic grinding wheel was controlled to about 1 drop every two seconds.

The dimpler of the invention has been described in somewhat general terms above. A more detailed description of some of the parts follows.

The axial light passage 46 in the stage 42 is filled at its upper end with a 0.25 inch (6.35 mm) glass plug which was ground from 7 mm Pyrex rod and epoxied in, after which it was lapped flush with the stage surface.

Figure 6:
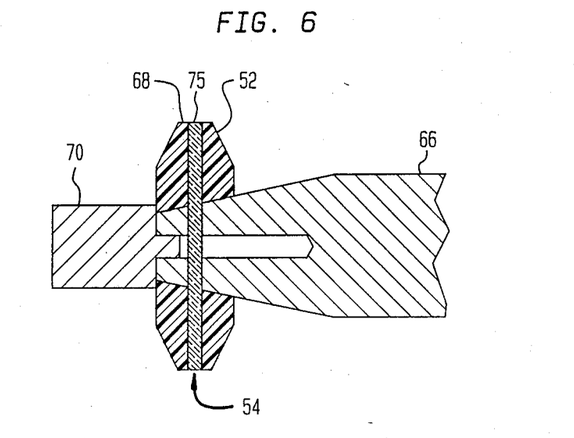
FIG. 6 is a cross-sectional view of a plastic grinding wheel and its shaft, taken along section VI—VI in FIG. 5.

As illustrated in FIG. 6, the plastic grinding wheel 52 (Gatan part number 656-0106) is fitted onto a conical end of a rotatable dimpler shaft 66. The plastic grinding wheel 52 has a partially spherical circumferential surface 68, that is, the annular circumference is equal to the wheel's circumference so that the surface 68 is in fact spherical with a radius of, for example, 7.5 mm. The dimpler shaft 66 can also be rotatably raised and lowered so as to bring the plastic grinding wheel 52 into contact with the mounted sample 16, as is standard on conventional dimplers. The plastic grinding wheel 52 is held to the dimpler shaft 66 with a retaining screw 70 screwed into the end of the shaft 66.

According to the invention, both the plastic grinding wheel 52 and the dimpler shaft 66 are drilled with diametric holes, for example, to a hole diameter of 0.031 inch (0.787 mm) with a #68 drill. The diametric holes are aligned to form the optical bore 54. The threaded portion of the conventional retaining screw 70 is shortened so as not to obstruct the optical bore 54.

When the chemical etchant was used, it seemed to block the propagation of light through the optical bore 54. To solve this problem and to ease alignment requirements, after the plastic grinding wheel 52 was mounted on the shaft 66, a piece 75 of optical fiber 14.5 mm long and 700 $\mu$m in diameter was prepared with polished square ends and was inserted into the bore 54 to loosely fit therein and was anchored to the bore 54 with Duco cement.

In order to be able to first mechanically grind a dimple and then to use the above plastic grinding wheel 52 with the optical fiber 75 for final chemical grinding, a separate grinding shaft and bearing housing assembly is dedicated to the plastic grinding wheel and is mounted on the dimpler after the rough mechanical grinding is completed.

Figure 7:
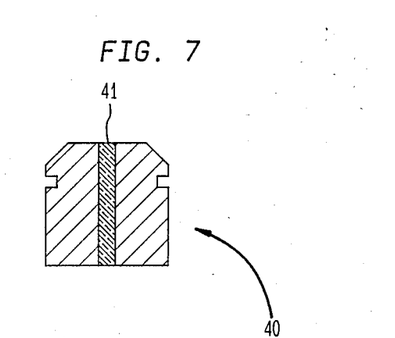
FIG. 7 is a cross-sectional view of a dimpler pin usable with the invention.

The dimpler pin 40, as illustrated in FIG. 7, has a main body of stainless steel type 303. The main body has a height of 0.370 inch (9.4 mm) and a diameter of 0.250 inch (6.35 mm). A top central surface has a diameter of 0.175 inch (4.4 mm) and has 45° beveled sides. A central axial hole is bored to a diameter of 1.5 mm and has epoxied therein a 1.5 mm diameter optical fiber 41. The ends of the fiber 41 are lapped flat with the pin surfaces. The sample being dimpled should be cemented over the fiber 41 with cement in order that the unperforated sample excludes ambient light from the fiber 41. The dimpler pin 40 is held in a 0.253 inch (6.43 mm) hole in the pin fixture 28 by a spring-load ball detente in the pin fixture 28. The sample 16 is mounted on the dimpler pin 40 while the preliminary planar mechanical thinning is performed.

Figure 8:
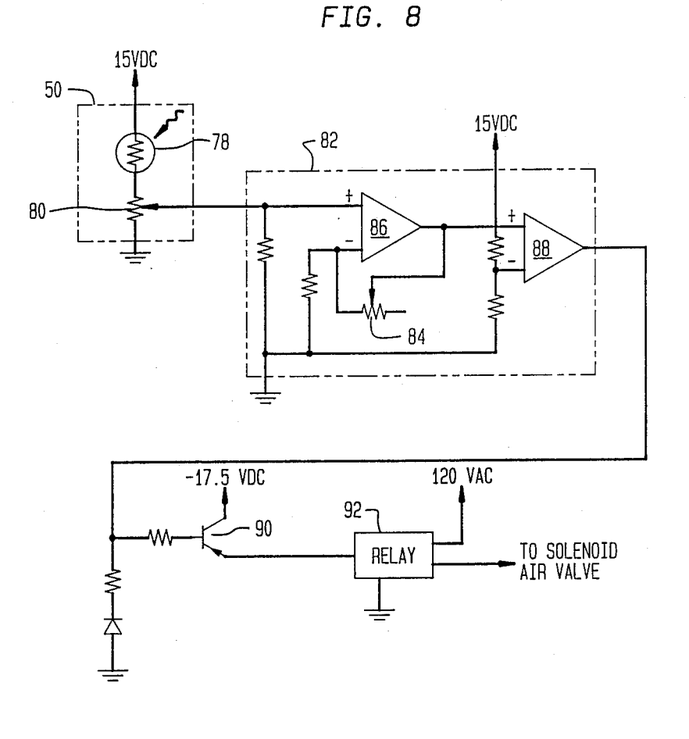
FIG. 8 is a schematic diagram of electronicss associated with the automatic termination of grinding with the dimpler of the present invention.

The optical detector 50 is illustrated in more detail in FIG. 8. A photoresistor 78 is mounted near the bottom of the dimple shaft 44. For example, the photo-resistor 78 may be the one supplied with the Gatan ion mill, Model No. VT5018424, having a diameter of 0.485 inch (1.23 cm). The photo-resistor 78 is biased between 15 VDC and ground in series with a 1 k$\Omega$ potentiometer 80. The adjustable tap of the potentiometer thus shows an increase in voltage when the sample 16 is perforated and light shines on the photo-resistor. An oscilloscope or AC voltmeter can monitor the chopped photo-resistor output.

In order to provide an automatic indication of perforation of a predetermined amount, a comparator-amplifier stage 82 receives the electrical output of the photo-detector 50. By changing the adjustable feedback resistor 84 of a first operational amplifier 86, acting as an amplifier, the gain of the amplifier may be changed. The threshold of a second operational amplifier 88, acting as a comparator, is determined by a resistor on its input. The sensitivity may be changed either by varying the gain with potentiometer 84 or by adjusting the photoresistor bias with potentiometer 80. Both amplifiers 86 and 88 may be of the 741 type. The effect is that the output of the second operational amplifier 88 sharply changes in the positive direction when a predetermined amount of light shines through the sample 16. It is possible to set the gain high enough that the comparator threshold voltage corresponds to a finite although thin thickness of a metallic or semiconducting sample.

The grinding can be automatically terminated by the use of electro-mechanical elements receiving the electrical output of the comparator-amplifier stage 82 and controlling the mechanical parts of the dimpler. The control-level signal from the comparator amplifier 88 controls a power transistor 90, such as a 2N6107 PNP transistor. This transistor 90 controls a relay 92, which switches 120 volt AC power to a solenoid air valve 94 controlling all the automatic mechanical movements. The 2N6107 transistor was not capable of driving an available solenoid or relay of sufficient capacity to directly switch the air solenoid air valve 94. Therefore, a two-stage relay 92 was used.

Figure 9:
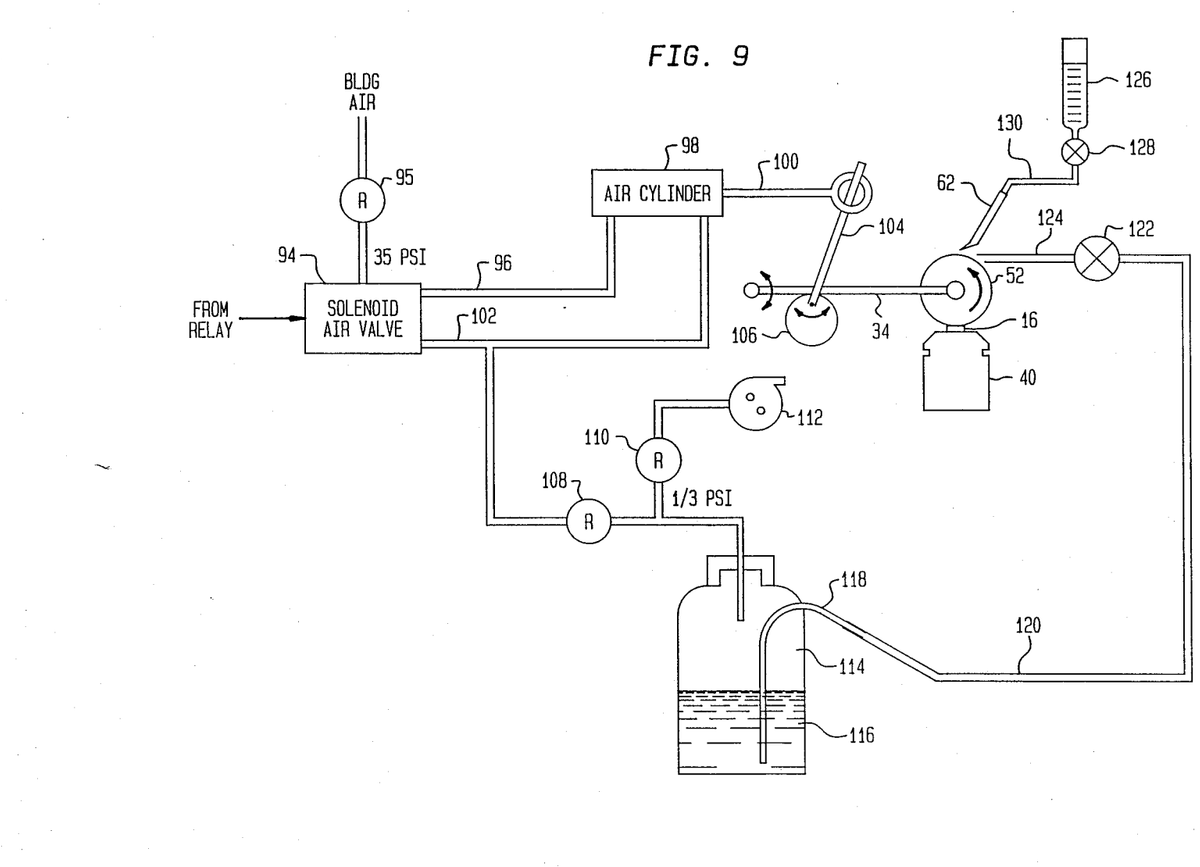
FIG. 9 is an illustration of the mechanical structure associated with the supply of chemical etchant and the automatic termination of etching.

The solenoid air valve 94, illustrated in FIG. 9, may be a Speedaire 1A209 equipped with port flow control valves (Speedaire 6X368) to limit the speed of piston movement. The air valve 94 receives building air regulated to 35 psi (181 mm Hg) by a regulator 95. When energized by the relay 92, the solenoid air valve 94 supplies positive pressure on a first air line 96 to an air cylinder (pneumatic actuator) 98 to extend its piston rod 100 and to thereby lower the grinding wheel 52. When not energized, the air valve 94 supplies positive pressure on a second air line 102 to retract the piston rod 100 and raise the grinding wheel 52. The air cylinder may be a double-acting 0.75" (1.9 cm) bore, 3.0" (7.6 cm) stroke cylinder Model 6498K153 available from McMaster. The cylinder piston rod 100 is slidably coupled to a handle 104 of a cam shaft 106, both of which are part of the commercially supplied dimpler. The coupling is accomplished by means of a sleeve loosely fitting the end of the handle 104 and rotationally joined to the end of the piston rod 100 by, for instance, a model 6498K41 clevis assembly from McMaster. The lifting cam 106 contacts the arm 34 holding the grinding wheel 52 to thereby lift the grinding wheel 52 when the piston rod 100 is retracted.

The second air line 102 also energizes a methanol flushing rinse system. The air pressure is reduced by a lower pressure air regulator 108 to a pressure somewhat less than 5 psi (26 mm Hg). A $\frac{1}{3}$ psi (1.7 mm Hg) check valve 110 (Nupro, B-4C-$\frac{1}{3}$) bleeds off most of this air pressure. A rotary ball flowmeter 112 used to monitor the flow as the check valve 110 is opened just enough to let the meter ball begin to spin. This low pressure is used to pressurize a rinse reservoir 114, which is a capped 500 ml Nalgene was bottle, partially filled with the methanol rinse 116. A spout 118 of the wash bottle 114 is pressed into $\frac{1}{4}$" (6.45 mm) Tygon tubing 120 at the end of which is a syringe stopcock (Leurlock) 122 connected to a $1\frac{1}{2}$" (3.8 cm) stainless steel needle 124. The needle 124 is directed to the top of the grinding wheel 52. Thereby, when perforation occurs, not only is the wheel 52 raised, but also the sample is immediately flushed with the methanol rinse 116 so as to immediately stop the chemical etching. The rinse occurs efficiently with the methanol rinse supplied to the wheel top only. The brominated methanol etchant is gravitationally supplied from a 50 ml burrette 126, manually controlled by a Teflon stopcock 128. The $Br_2$/methanol etchant is supplied via Tygon tubing 130 to the drawn glass pipette or drip tube 62 positioned over the rotating wheel 52 at sufficient distance to not contact it when the wheel 52 is automatically lifted.

The invention is not limited to the embodiment described above and many variations are easily developed. The optical detection can rely on differences in reflectivities between the sample being ground and the grinding wheel. In this case, an optical path needs to be provided only in the stage.

For chemical etching with the wheel, different etchants and different wheel materials may be used. The rinse could be supplied by the same tube as the etchant. The etchant supply could be terminated automatically. The pneumatic actuators could easily be replaced by electrical motors, solenoids, or other electrical components. A laser is not required for the light source. The photodetector need not be a photoresistor and the electronics can be widely varied.

Other variations within the scope of the invention should be obvious to those skilled in the art.

GENERAL PROCEDURE

A general procedure was developed which appeared well suited to dimpling and transferring samples of compound semiconductors for TEM cross-sectional imaging. The invention is, however, not limited to this procedure and several examples presented below did not follow the entire general procedure.

1. PRELIMINARIES

In our general procedure, both the dies 10 and the supports 14 are selected from the diced fragments of the same wafer. All the pieces were bonded face-to-face with EFFA Epox 812 in a 1:1 mixture and thereafter cured at 120° C. for 12 hours.

Figure 10:
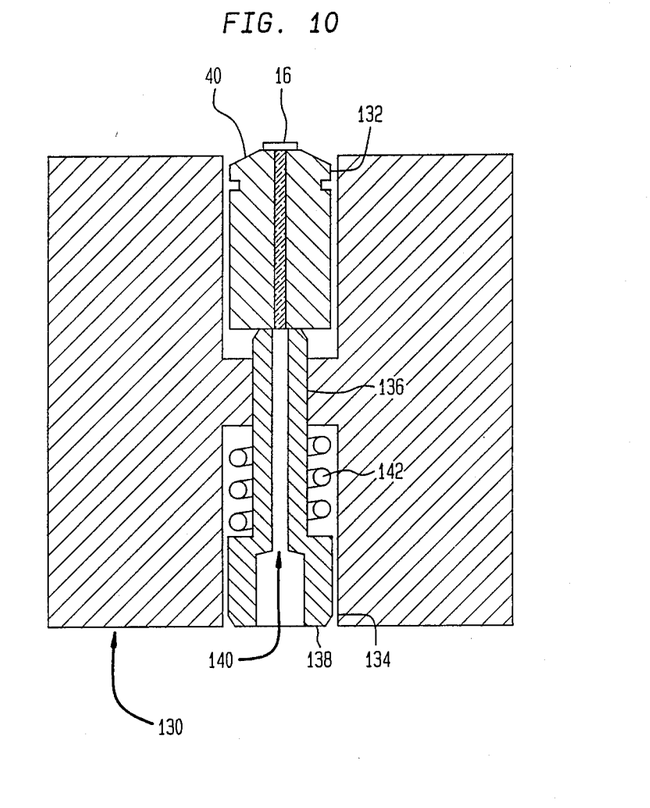
FIG. 10 is a cross-sectional view of a polishing fixture useful in preparing a sample for the dimpler and for other procedures.

The dimpler pin 40 of FIG. 7 is placed in a 1" polishing fixture 130 (described below) and these are placed on a hot plate at about 140° C. Crystalbond #509, manufactured by Aremco Products, Inc. is a thermoplastic polymer used for stable mounting. A drop of Crystalbond is applied to the top of the pin 40 and the sandwich structure is positioned on top thereof on edge. After cooling, the polishing fixture 130, pin 40 and sample 16 are placed in a polishing ring and the top of the sample 16 is flattened with wet silicon carbide papers from #240 through #600 grit. The sample 16 is then rinsed and, being returned to the hot plate, is removed from the pin 40 and flipped over so as to expose the opposite side. The other side of the sample 16 is then flattened in the same way so as to produce two parallel faces.

The polishing fixture 130 is illustrated in cross-section in FIG. 10 and has been found useful in conjunction with handling the pin-mounted sample. It is made of 316 stainless steel, has a generally cylindrical shape with a diameter of 1 inch (2.54 cm) and a height of 1.025 inches (2.6 cm). A pin bore 132 and a screw bore 134 are drilled to a diameter of 0.253 inch (6.426 mm) and respective depths of 0.420 inch (10.67 mm) and 0.39 inch (9.906 mm). A central connecting bore 136 is tapped to #10-24. A #10-24 stainless-steel socket-head machine screw 138 with an overall length of 0.65 inch (1.65 cm) has an axial vent hole 110 drilled to a diameter of 0.081 inch (2.06 mm) with a #46 drill. The vent hole 140 serves both as a vacuum release hole and a path for illumination from the socket-screw side. The socket-head screw 138 is screwed into the connecting bore 136 and is held tightly therein by a locking spring 142 of 0.039 inch (0.99 mm) stainless-steel spring wire.

The dimpler pin 40 is fit into the pin bore 132 and its position is adjusted with the socket-head screw 138. The optical fiber 41 of the dimpler pin 40 lines up with the vent hole 140 of the socket-head screw 138.

2. FIRST DIMPLE

The pin with the attached sample is transferred to the dimpler and the dial gauge is zeroed on top of the sandwich with the bronze grinding wheel attached to the grinding shaft. With use of the dimpler's alignment microscope, the sample is centered with the epoxy layer coincident with the centering dot of the microscope.

Preliminary mechanical grinding is performed by cutting a dimple to a depth of 40 to 60 $\mu$m with 2 to 4 $\mu$m diamond paste. The dimpler depth gauge is used to monitor the depth. The dimple surface is then polished with 0.3 $\mu$m alumina slurry and a felt wheel. The polishing is finished with a quick bromine etch of about one minute another felt wheel. During the above procedure, the down pressure is maintained in the range of 20 to 22 grams of the dimpler, as set on the dimpler counterweight. In the bromine etch, the felt wheel is saturated with methanol and then lowered onto the sample, whereafter the bromine-methanol solution is dispensed by the pipette. After the bromine etch, the sample is rinsed with methanol.

The above procedure removes the scratches resulting from the diamond paste while removing an additional ~5 $\mu$m of material. The total depth of the dimple must be closely controlled in order to perform the second dimpling step.

3. SECOND DIMPLE

The pin is removed from the dimpler stage, replaced in its polishing fixture 130, and placed on the hot plate. After the Crystalbond is melted, the sample is removed and the pin cleaned with solvent. The top pin surface, without the sample, is used to zero both a height gauge associated with the mounting apparatus and the depth gauge of the dimpler. The pin is then returned to the grinding fixture and hot plate and the sample is mounted thereon, dimple-side down, with Crystalbond. To prevent entry of ambient light during optically controlled dimpling, the sample must be centered on the fiber 41 of the dimpler pin 40. Furthermore, air bubbles must be excluded from the dimple as it is placed face down on the dimpler pin 40. The sample and pin are allowed to cool. Any minor adjustments to the position of the sample during cooling may be made with the tip of a wooden stick.

The sample so mounted on the dimpler pin is thinned on wet sandpapers until it is about 100 $\mu$m thick, as measured by the previously described height gauge. This distance will include about 5 $\mu$m of the Crystalbond. If the first dimple was 55 $\mu$m deep, then there remains 40 $\mu$m remaining to be ground after thinning to the measured 100 $\mu$m. The pin with mounted sample is then centered again on the dimpler so that the new center coincides with the center of the first dimple.

A 30 $\mu$m dimple is now mechanically cut. It is preferred that in the softer materials the roughest grinding be done with the bronze wheel and a little 0.3 $\mu$m alumina. Alumina produces less surface damage than 2–4 $\mu$m diamond paste with little increase in cutting time. The second dimple may be cautiously polished with felt and alumina although this is not always necessary. At this point, there is less than 10 $\mu$m of material remaining.

4. PERFORATION

The mechanically cut second dimple is then carefully cleaned with a cotton-tipped wooden swab and deionized water mixed with detergent. The bearing assembly used for mechanical grinding is demounted from the dimpler and replaced with the one having the plastic cutting wheel and optical bore. The methanol rinse jet, bromine-methanol drip tube and aspirator tube are placed in position. The down pressure is set at 18.5 grams.

The plastic grinding wheel is lubricated with a few drops of methanol and lowered into the sample. Its rotation rate should be slow, about 120 rpm. The bromine-methanol solution is then allowed to drip at one-half drop per second. The laser is turned on and a visual inspection made to verify correct focusing on the wheel perimeter.

With the amplifier gain set at maximum for a minimum sized perforated hole, it takes about five minutes for perforation to occur under the above conditions. The dimpling is automatically terminated when the wheel slightly lifts and the methanol rinse jet bathes the wheel and sample is methanol. The operator manually turns off the bromine drip and thereafter shuts off the needle jet valve for the rinse. The operator then moves the grinding wheel arm completely out of the way. The dimpler pin may be removed for microscopic inspection of the perforated sample. If further etching is deemed necessary, the above procedure can be repeated for a fixed time. Alternatively, the amplifier gain can be reduced or the bias reduced across the photoresistor and then automatic termination is again relied upon.

5. TRANSFER

The sample must now be removed from the dimpler pin without damaging its extremely delicate, ultrathin areas.

The pin with the attached sample is placed in the grinding fixture. The following work is preferably performed under a stereo microscope. A molybdenum ring is prepared from a ring used for mounting of TEM samples. This ring is formed photolithographically from a molybdenum sheet. There are four radial tabs extending from the ring. To prepare the molybdenum ring, three of the four tabs are removed and the remaining tab is bent at 90° to form a handle. This ring, exclusive of the tab handle, measures 3 mm OD×1 mm ID×50 $\mu$m. One drop of each of the two components of Devcon 5 minute epoxy resin are squeezed onto a clean microscope slide, are mixed and spread with a stick over the slide. With tweezers, the molybdenum ring is placed on the epoxy to float thereupon and is then lifted off to be placed on a dry part of the slide. The molybdenum ring so wetted with epoxy is precisely placed around the dimple on the sample and gently pressed to the sample. The ring handle should be positioned ovr a portion of the sample extending beyond the ring. The fixture is placed on the hot plate to accelerate setting of the epoxy. The temperature is not allowed to rise beyond ~30° C. Thus, the fixture is warmed only slightly and is then removed.

After two hours of curing at no more than 30° C., the handle is removed by carefully bending the tabular handle back and forth. The handle must not be actually grasped but only pushed in alternate directions with no lifting or twisting force. Excess sample material is then trimmed away from outside of the molybdenum ring by scribing along the edge of the ring with a tungsten carbide wafer scriber. The sample material exterior to the scribe is broken away by lateral movements of the tip of the scriber. Further scribing should be substituted for excessive force if lateral pressure is initially unsuccessful.

At this point, the sample is generally circular and is mounted from below to the dimpler pin and from above to the molybdenum ring. The dimpler pin and attached items are stood in a 10 ml beaker and covered with warm solvent such as acetone. During several hours of soaking, the solvent penetrates through the perforation to dissolve the Crystalbond in the bottom dimple and then in the surrounding area. The sample with attached molybdenum ring eventually falls off the dimpler pin. No excessive force is applied to the ultrathin areas around the perforation. The sample and attached molybdenum ring are rinsed with clean solvent with all handling being done via the ring. Excess solvent is blotted away. The ring and sample can then be placed directly into the holder of the electron microscope.

EXAMPLE 1

An InP chip was mounted on the dimpler pin with a 25 μm thick, 100 mesh molybdenum grid in between. Crystalbond was used as an adhesive and was melted at 140° C. The so mounted chip was mechanically thinned to 0.004 inch (102 μm) with wet 320 and 400 paper. The pin was then mounted in the dimpler and a preliminary dimple was formed using 2-4 μm diamond on a bronze wheel using 22 grams of downward pressure. The grinding left about 30 μm of InP at the bottom of the dimple. The surface was polished with a felt wheel and 0.3 μm alumina at the same pressure and speed.

The optically controlled grinding wheel was then installed on the dimpler and dimpling proceeded with about 16 grams down pressure and the bromine-methanol etchant. After about five minutes of grinding, the optical control system automatically cut off the grinding and rinsed the sample with methanol.

The sample was removed from the pin by gluing with epoxy a 3 mm molybdenum ring to the top of the sample and then soaking the sample in warm acetone until it fell off.

The quality of the perforation was excellent. It was formed on the interface and had smooth edges. The optical interference rings around the perforation demonstrated the thinness of the surrounding area.

EXAMPLE 2

The second example involved thinning a multi-layer structure of ZnSe/GaAs on a GaAs substrate. One surface was cleaned and polished. The polished side was then mounted on the 100 mesh molybdenum grid. After the sample was mechanically thinned to a planar thickness of 100 μm, a dimple was cut first with diamond paste, then with 0.3 μm alumina and a bronze wheel and polished with felt.

The bromine-methanol dimpling with the plastic grinding wheel was then performed with 18 grams of down pressure. Perforation occurred after about 5 minutes and was automatically stopped. The perforation was very small but it was felt that the border around the hole was too thick for TEM. Therefore, the sample was returned to the dimpler. The bias voltage on the photoresistor was reduced and bromine etching was continued for about 10 to 15 second before the dimpler automatically stopped.

The results were again very good. The perforation was centered on the interface and showed smooth, sharp edges.

The above two examples using a grid showed effective perforation. However, much difficulty was experience in separating the sample from the grid and transferring it to a TEM ring holder without breaking the wedge-like ultrathin areas. Therefore, the double-dimpling technique described in the general procedure above was developed and the following examples were performed to verify the double dimpling.

EXAMPLE 3

This example demonstrated the consistency of centering between changed bearing assemblies of the dimpler when both mechanical and chemical grinding was performed.

A single fragment 2.5 mm×2.5 mm of GaAs was adhered on its principal face to the dimpler pin with Crystalbond. The sample was thinned to 0.0036 inch ($\approx$90 μm). A dimple was then mechanically ground to a depth of about 60 μm on one side with the bronze wheel and 2-4 μm diamond paste. There was no alumina polishing.

The bearing assembly on the dimpler was then changed to the one mounting the optical plastic wheel. Chemical grinding with a strong brominated methanol etchant was begun. After about 5 minutes, the dimpling was automatically stopped by the optical control equipment.

Visual inspection of the perforation showed a circular hole with clean edges. There was no indication of any lack of alignment between the mechanical and chemical etching, that is, between the two bearing assemblies.

EXAMPLE 4

A planar piece of GaAs was used similarly to that in Example 3. On a first side, a dimple was mechanically cut to a depth of about 50 μm with a bronze wheel and diamond paste. It was then polished with 0.3 μm alumina and finally etched with a felt wheel onto which was dripped Br$_2$ in methanol. The final depth of the dimple was about 60 μm.

The sample was removed from the dimpler pin, flipped, and remounted according to the technique described in the above general procedure. The sample was planar thinned to 0.0047 inch (120 μm) as measured away from the dimple. The sample was recentered on the dimpler and a second dimple on the second side was mechanically cut to a depth of about 35 µm with diamond paste.

The bearing assembly on the dimpler was changed to the one with the optical plastic wheel. Chemical etching was then initiated and automatically terminated. The bromine etchant was manually applied and the rinse manually performed. Visual inspection under a microscope showed very clean edges to the perforation.

In this example, we attempted to dispense with the bonding to the molybdenum ring. The pin and sample were soaked for about 20 minutes in acetone. The GaAs sample fell off the pin without damage to the edges of the perforation. However, direct handling of the sample without the ring and ring handle proved difficult and the sample was dropped and broke.

As should be clear from the above detailed description and the examples, the dimpler of the present invention offers many advantages over the prior art. For many types of materials, it allows preparation of ultra-thin samples without the use of ion milling. The perforations are well defined and their positions are easily controlled. The samples are not subjected to potentially deleterious ion bombardment. These advantages are realized with fairly simple modifications to conventional dimplers.

What is claimed is:

1. A dimpling apparatus for forming a dimple in a sample, comprising:
   a stage rotating about a first axis having a first light passage extending along said first axis and for holding a sample adjacent said first light passage;
   a wheel contactable with said held sample and rotating about a second axis perpendicular to said first axis and having a second light passage extending at least partially along a radial direction of said wheel and connecting to a circumference of said wheel, an interruptible light path being formed at least partially by said first light passage and said second light passage and being interrupted by a rotation of said wheel;
   a light source arranged at a first end of said light path; and
   a light detector arranged at a second end of said light path.

2. A dimpling apparatus as recited in claim 1, wherein said light source comprises a laser.

3. A dimpling apparatus as recited in claim 1, further comprising:
   threshold means connected to an output of said light detector for determining when said output exceeds a predetermined level, to thereby indicate a predetermined degree of perforation or near perforation of said sample by said wheel.

4. A dimpling apparatus as recited in claim 2, further comprising means for removing said wheel from contact with said held sample responsive to an output of said threshold means.

5. A dimpling apparatus as recited in claim 4, further comprising:
   a source of an etchant for etching said sample and applied to said rotating wheel; and
   means for inhibiting said etching of said etchant responsive to said threshold means.

6. A dimpling apparatus as recited in claim 1, further comprising a source of an etchant for etching said sample and applied to said rotating wheel.

7. A dimpling apparatus as recited in claim 6, wherein said etchant comprises a solution of a halogen and an alcohol and said sample comprises a compound semiconductor.

8. A dimpling apparatus as recited in claim 1, wherein said second light passage comprises a diametric bore passing radially through said wheel and further comprising an optical fiber inserted in said bore.

9. A dimpler, comprising:
   means for holding and rotating a sample;
   a rotating wheel contactable with said sample;
   optical means irradiating a light beam on a contact area between said wheel and said sample while said rotating wheel is in contact with said rotating sample; and
   a photodetector receiving light produced from an interaction of said light beam with said contact area.

10. A dimpler as recited in claim 9, further comprising:
    stopping means responsive to an output of said photodetector for stopping a rotating contact of said wheel with said sample.

* * * * *